United States Patent [19]

Van Dyne

[11] Patent Number: 5,575,764
[45] Date of Patent: Nov. 19, 1996

[54] PROSTHETIC JOINT WITH DYNAMIC TORQUE COMPENSATOR

[76] Inventor: Leonard A. Van Dyne, 2638 Oakmont Dr., W. Harrison, India. 47060

[21] Appl. No.: 355,605

[22] Filed: Dec. 14, 1994

[51] Int. Cl.$^6$ .................................................. A61F 5/00
[52] U.S. Cl. .............................. 602/26; 602/16; 482/124
[58] Field of Search ................................. 602/5, 16, 20, 602/23, 26, 32, 36–38; 482/120, 121, 124, 127; 601/23, 26, 33, 34

[56] References Cited

U.S. PATENT DOCUMENTS

| | | | |
|---|---|---|---|
| 2,706,297 | 4/1955 | Sartin et al. | 602/16 X |
| 4,370,977 | 1/1983 | Mauldin et al. | 602/16 |
| 4,397,308 | 8/1983 | Hepburn | 602/16 |
| 4,485,808 | 12/1984 | Hepburn | 602/16 |
| 4,508,111 | 4/1985 | Hepburn | 602/16 |
| 4,538,600 | 9/1985 | Hepburn | 602/16 |
| 4,657,000 | 4/1987 | Hepburn | 602/16 |
| 4,865,024 | 9/1989 | Hensley et al. | 602/16 |
| 4,944,290 | 7/1990 | Hepburn | 602/16 |
| 4,947,835 | 8/1990 | Hepburn et al. | 602/16 |
| 5,002,045 | 3/1991 | Spademan | 602/16 |
| 5,058,574 | 10/1991 | Anderson et al. | 602/16 |
| 5,070,868 | 12/1991 | Hepburn et al. | 602/16 |
| 5,107,824 | 4/1992 | Rogers et al. | 602/16 |
| 5,117,814 | 6/1992 | Luttrell et al. | 602/16 X |
| 5,230,696 | 7/1993 | Silver et al. | 602/16 |
| 5,285,773 | 2/1994 | Bonotti et al. | 602/16 X |
| 5,395,304 | 3/1995 | Tarr et al. | 602/16 X |
| 5,399,154 | 3/1995 | Kipnis et al. | 602/26 |
| 5,437,611 | 8/1995 | Stern | 602/16 |
| 5,456,268 | 10/1995 | Bonutti | 602/16 X |
| 5,472,410 | 12/1995 | Hamersly | 602/16 |

Primary Examiner—Richard J. Apley
Assistant Examiner—Kim M. Lee
Attorney, Agent, or Firm—Wood, Herron & Evans, P.L.L.

[57] ABSTRACT

A constant torque joint utilizes joint elements extending respectively between brace attachments for use in an anatomical brace. The brace has a range of motion dependent upon the particular application and in one embodiment from about 65° to about 215° with an included angle of motion of approximately 150°. A constant torque in the joint is provided by a spring-loaded cable wherein a cam driven cable anchor pin is utilized to compensate for variations in the spring cable joint system to produce a constant torque within the joint throughout the full range of motion of the joint.

29 Claims, 3 Drawing Sheets

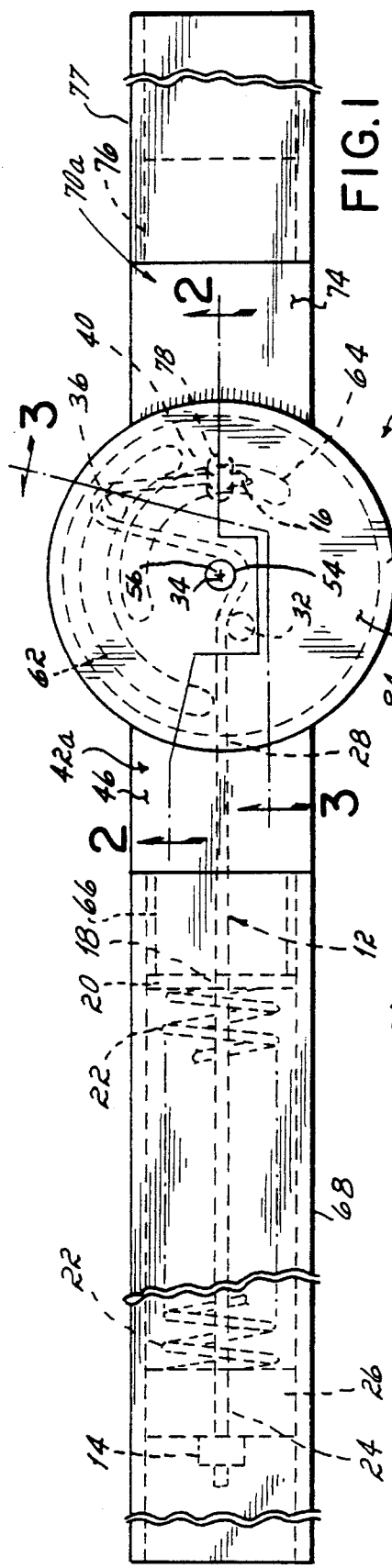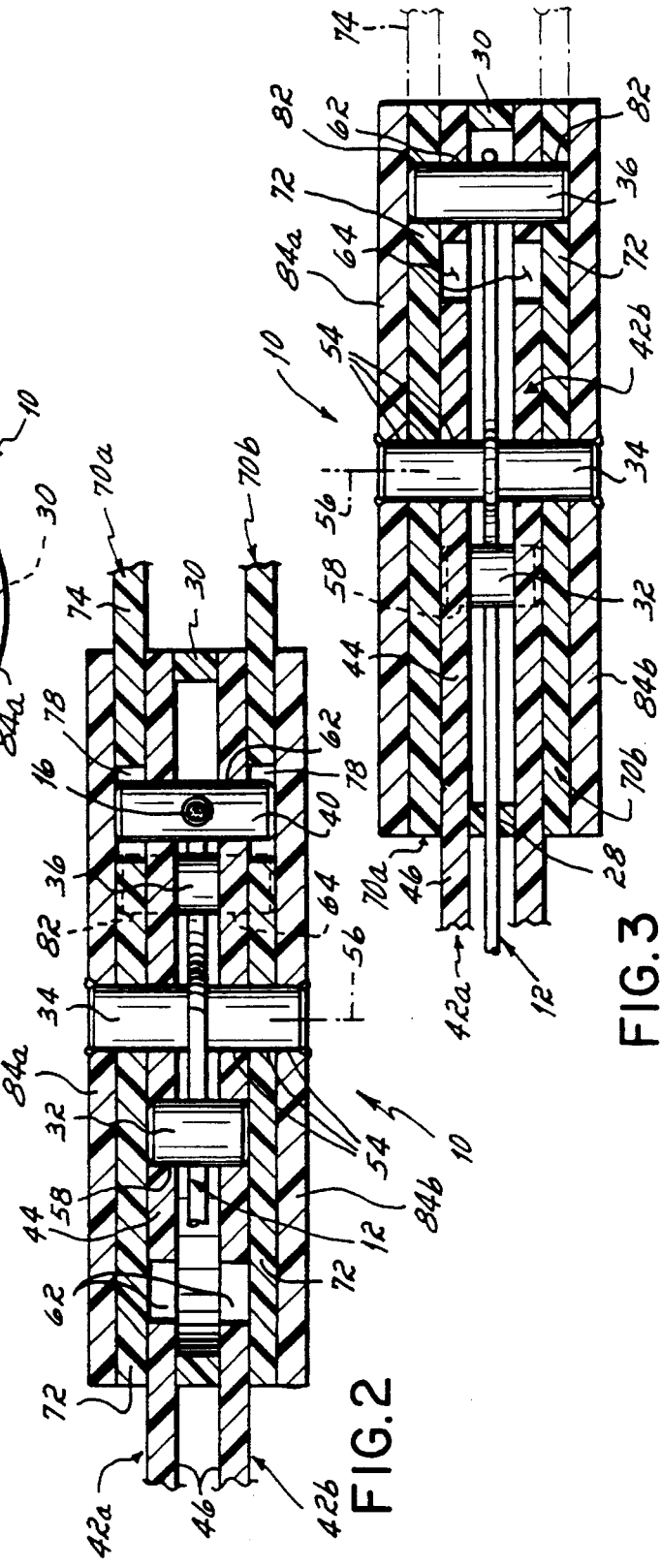

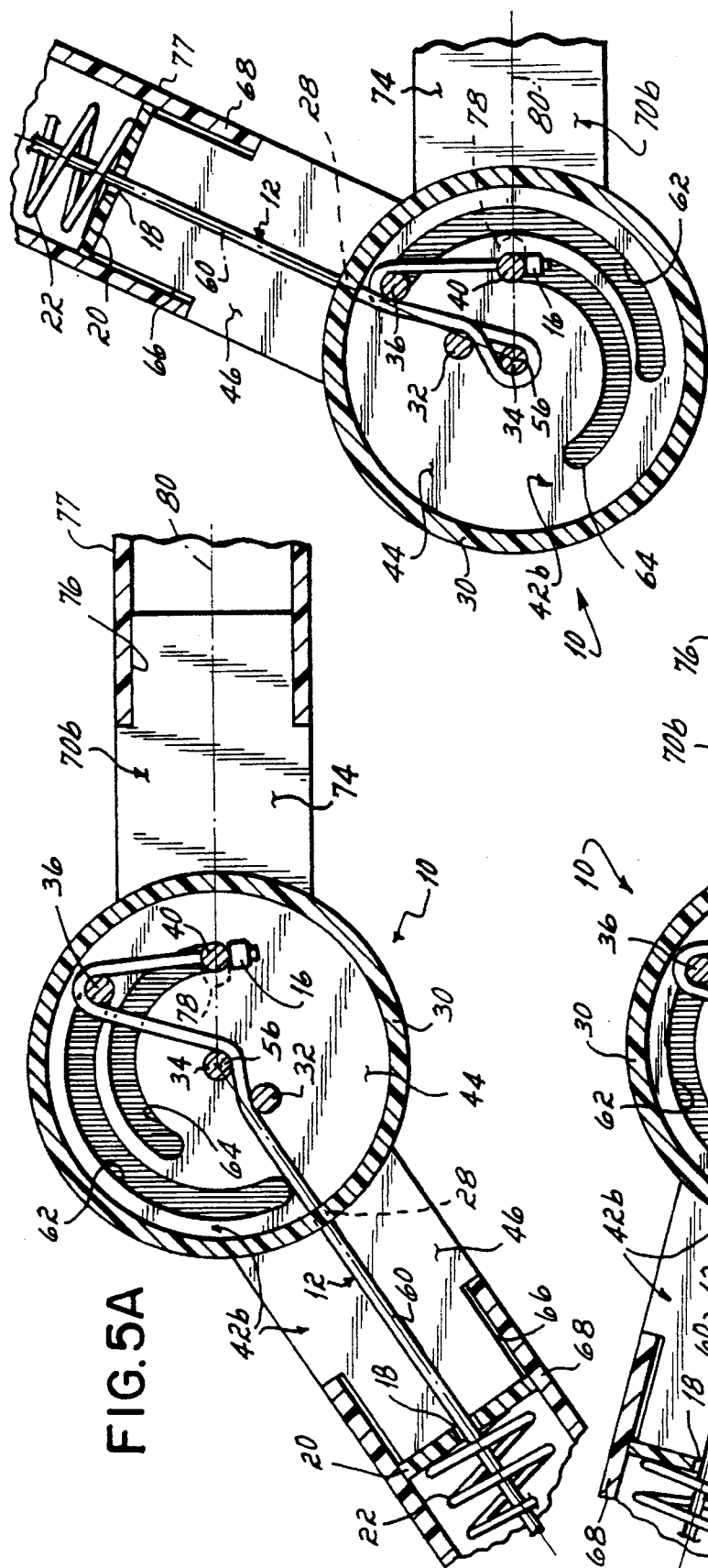

PROSTHETIC JOINT WITH DYNAMIC TORQUE COMPENSATOR

BACKGROUND OF THE INVENTION

This invention relates to mechanical prosthesis and particularly to a constant torque joint for anatomical braces.

In the past, treatment for various muscular, skeletal or nervous conditions has included the utilization of particular anatomical braces which are applied to a patient's appendage and which either supports that appendage or which provide a rehabilitative measure of resistance to movement of that appendage. In this way, the patient's muscular, skeletal or nervous system can be exercised and used with a view toward rehabilitation.

While a variety of different types of such braces have been provided, the currently available structures have certain inherent disadvantages. For example, while the braces may provide an adequate range of motion, they do not provide for constant resistance or torque over that range of motion; and thus, the maximum rehabilitative benefit of the exercise is not realized. Even where certain springs are utilized in an effort to provide a constant torque or resistance to motion of the joint between two different parts of the brace, the vagaries of spring rates, spring manufacturing, spring materials, and system friction or other forces impede a result of constant torque or resistance.

Accordingly, it has been an object of this invention to provide a constant torque joint for an anatomical brace such that a constant resistance to motion is applied by the joint connecting two different portions of the brace movable with respect to each other throughout the entire range of movement thereof.

It has been another objective of the invention to provide an anatomical brace having a constant torque throughout its full range of motion.

It has been another objective of the invention to provide a compensator for accommodating system foibles toward the goal of producing a constant torque or constant resistance to the joint for use in rehabilitation.

It has been another objective of the invention to provide a constant torque coupling.

SUMMARY OF THE INVENTION

To these ends, a preferred embodiment of the invention contemplates the utilization of a spring-powered torque-producing cable combined with a dynamic torque compensator for minimizing torque variations of the joint throughout its full range of movement. In particular, a preferred embodiment of the invention includes a torque-producing cable connected to a compression spring, wherein another end of the cable is threaded about a variety of pins associated with the pivot point of the joint such that a constant torque is produced by the joint by virtue of the cable wrapping about a center or pivot pin and anchored by a free floating anchor pin. The anchor pin is cam driven to compensate for spring and other system variations so that the end result is a constant torque or constant resistance joint where a constant torque is provided throughout the full range of motion.

In a preferred embodiment, for example for use in connection with an elbow, the range of motion of the joint is approximately through 150° beginning at a 65° separation of the two brace extensions and terminating at about 215° separation thereof. It will be appreciated that other ranges of motion are available with the joint of this invention for different body joints. The results are obtained through the utilization of an arcuate slot accommodating a pulley pin and through the utilization of a floating anchor pin travelling within a radial slot and being driven by means of an arcuately shaped eccentric cam. The configuration of the arcuately shaped eccentric cam is a function of the non-linearity of the spring response and the compensation for it as to be described herein. As the joint moves through its various positions, the resulting torque, or resistance to motion is maintained at a constant level as the cable is wrapped about the pivot pin and a moment arm of the joint varies as the anchor pin translates within the radial slot.

The invention produces a joint which can be used, for example, in an elbow brace for accommodating motion from a fully open position, accommodating an angular orientation of about 215° between the extensions of the brace on each side of the joint to a fully closed position of about 65° between those two members. The range of motion of the joint accommodates the typical full range of an anticipated elbow rotation and provides a constant torque or resistance against motion throughout that entire range. Such a constant torque joint is provided, while at the same time maintaining the joint in a very small package so that the brace itself can be relatively small and easily used.

BRIEF DESCRIPTION OF THE DRAWINGS

The advantages and objectives of the invention will become more readily apparent from the following description of the details of a preferred embodiment of the invention and from the drawings in which:

FIG. 1 is a top plan view of a joint with a dynamic torque compensator according to this invention;

FIG. 2 is a side cross-sectional view taken along line 2—2 of FIG. 1;

FIG. 3 is a side cross-sectional view taken along line 3—3 of FIG. 1;

FIGS. 5A through 5C are top cross-sectional views of the joint with the extensions in various angular relationships relative to one another.

DETAILED DESCRIPTION OF A PREFERRED EMBODIMENT

Figure 4:
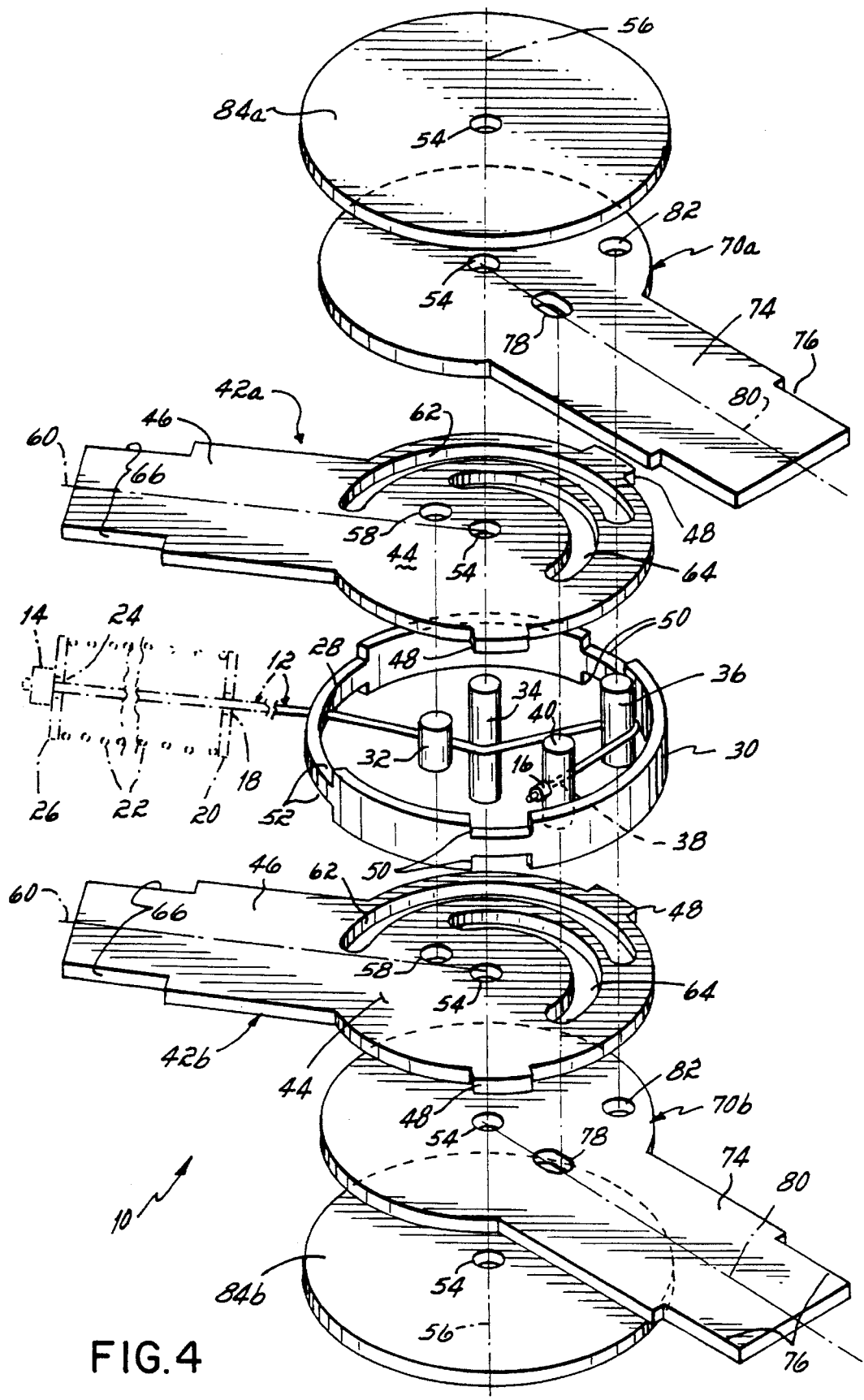
FIG. 4 is an exploded perspective view of the components of a preferred embodiment of the invention.

A perspective view of a prosthetic joint 10 with a dynamic torque compensator is shown in FIG. 4. The invention is described herein and shown in the drawings in a particular embodiment, as for example a joint for use in rehabilitating an elbow joint; however, other configurations and embodiments are possible and within the scope of the invention. The joint 10 includes a torque cable 12 secured at first and second ends by a collar 14, 16, respectively. A first end of the cable 12 passes through a hole 18 in a fixed stop plate 20, the center of a helical compression spring 22, and a hole 24 in a movable abutment plate 26. The collar 14 is juxtapositioned to a face of the movable abutment plate 26 opposite from the spring 22. The cable 12 passes through the spring 22 and stop plate 20 and through a hole 28 within a side wall of a generally circular bushing 30. After entering the bushing 30 through the hole 28, the cable 12 wraps around a face of a tangent pin 32 and then around an opposite face of a center pivot pin 34. The cable 12 then passes around a traveling pulley pin 36 and passes through a hole 38 in an anchor pin 40. The collar 16 is juxtapositioned on an opposite side of the anchor pin 40 to secure the cable 12 thereto. The cable 12 is shown as having a first end terminating at the movable abutment 26 and a second end terminating at the anchor pin 40. However, it will be appreciated that both ends of the cable 12 could be secured to the movable abutment 26 with the cable 12 folded back on itself and each portion thereof passing through the spring 22 and the bushing hole 28, around the respective pins as indicated and looped around the anchor pin 40 thereby avoiding the need for the collar 16 securing an end of the cable 12 to the anchor pin 40. Routing the cable 12 in this manner alleviates the need for the hole 38 in the anchor pin 40, thereby providing a more structurally sound anchor pin 40 which is less prone to failure. Likewise, the cable 12 is of a double thickness over most of its length, thereby providing a stronger cable within the joint 10 of this invention.

The cable 12 and bushing 30 are sandwiched between an upper and a lower generally planar moving plate 42a, 42b, respectively, in a presently preferred embodiment of the invention. The upper and lower moving plates 42a, 42b are identically configured and aligned and each include a generally circular portion 44 and a generally rectangular arm 46 extending therefrom. The upper and lower moving plates 42a, 42b and the bushing 30, when assembled, are fixed relative to each other by tabs 48 which project from a perimeter edge of the circular portion 44 of each moving plate 42a, 42b. The tabs 48 are seated within notches 50 in the upper and lower edges of the bushing 30. Similarly, enlarged notches 52 are provided on the upper and lower edges of the bushing 30 to accommodate the arms 46 projecting from the circular portions 44 of the upper and lower moving plates 42a, 42b when the bushing 30 is sandwiched therebetween.

The moving plates 42a, 42b each include a pivot pin aperture 54 centrally located within the circular portion 44 thereof and along a pivot axis 56 of the joint 10. The moving plates 42a, 42b also include a tangent pin aperture 58 spaced from the pivot pin aperture 54. The pivot pin 34 and tangent pin 32 extend through the pivot pin aperture 54 and tangent pin aperture 58, respectively, to fix the position of the pins relative to the moving plates. The tangent pin 32 and aperture 58 are located to maintain the cable 12 in contact with the pivot pin 34 as the joint 10 is pivoted. In a preferred embodiment, the cable 12 between the tangent pin 32 and the stop 20 is positioned along a centerline 60 of the moving plate arms 46.

The moving plates 42a, 42b also include an arcuate cam slot 62 proximate the perimeter of the generally circular portion 44. In a presently preferred embodiment, the arcuate cam slots 62 in the upper and lower moving plates 42a, 42b capture the pulley pin 36 therein and enable the pulley pin 36 to pass through an arc of approximately 150°. The arcuate cam slots 62 begin at approximately the centerline 60 of the arm 46 in each of the moving plates 42a, 42b and extend proximate a perimeter edge of the circular portion 44 through an angle of about 150°. The arcuate cam slot 62 is a constant distance away from the pivot axis 56 of the joint 10 which extends through the pivot pin 34 and the pivot pin aperture 54.

The upper and lower moving plates 42a, 42b each also include an eccentric cam slot 64 which captures the anchor pin 40 therein. The eccentric cam slot 64 in a presently preferred embodiment enables the anchor pin 40 to travel through an arc of approximately 150°. The eccentric cam slot 64 is eccentrically positioned relative to the pivot axis 56 of the joint 10 so that one end of the eccentric cam slot is more closely spaced relative to the pivot axis 56 than a second end thereof. Therefore, as the anchor pin 40 travels within the eccentric cam slot 64, the separation between the pivot axis 56 and the anchor pin 40 increases or decreases depending on the direction of travel.

A terminal end of each arm 46 of the moving plates 42a, 42b has a ledge 66 on each side edge thereof. Each ledge 66 is configured to accommodate a side plate 68 positioned perpendicular to the arm 46, the stop 20 and moving abutment 26 as shown in FIG. 1. With the upper and lower moving plates 42a, 42b sandwiched around the bushing 30, the side plates 68 are seated within the ledges 66 on the arms 46 of the moving plates 42a, 42b and the spring 22, stop 20, and abutment 26 are positioned between the side plates 68 (FIG. 1).

Similarly configured upper and lower stationary plates 70a, 70b, respectively, are juxtapositioned to the upper and lower moving plates, 42a, 42b, respectively, as shown in FIGS. 2–4. Each stationary plate 70a, 70b also includes a generally circular portion 72 and a rectangularly shaped arm 74 extending from the perimeter thereof. A terminal end of each arm 74 includes ledges 76 on opposite side edges thereof. In a preferred embodiment of the invention, the diameter of the circular portions of the stationary plates 70a, 70b and the moving plates 42a, 42b are equal. The stationary plates 70a, 70b include pivot pin apertures 54 centrally located within the circular portions 72 and capturing the pivot pin 34 along the pivot axis 56 of the joint 10. The upper and lower stationary plates 70a, 70b also include a radial slot 78 capturing the anchor pin 40 and permitting the anchor pin 40 to travel along a radius of the circular portion 72 projecting from the pivot axis 56 and pivot pin aperture 54. The radial slot 78 is aligned in a preferred embodiment along a centerline 80 of the arm 74 which passes through the pivot pin aperture 54. However, the radial slot 78 could be in a different location on the stationary plates 70a, 70b within the scope of this invention. The movement of the anchor pin 40 within the radial slot 78 corresponds to the changing length of the moment arm within the joint 10. The changing moment arm length compensates for the non-linearity of the spring rate to provide a constant torque joint 10 as described in detail later herein.

A pulley pin aperture 82 is positioned proximate a perimeter edge of the circular portion 72 of each stationary plate 70a, 70b. The pulley pin aperture 82 is positioned approximately 30° from the centerline 80 of the arm 74.

An upper and a lower circular cap plate 84a, 84b, respectively, are positioned on the top and bottom surfaces of the joint 10, respectively. Each cap plate 84a, 84b includes a pivot pin aperture 54 centrally located therein along the pivot axis 56 of the joint 10. The upper and lower cap plates 84a, 84b sandwich the stationary plates 70a, 70b, moving plates 42a, 42b, and bushing 30 therebetween. It will be appreciated by one of ordinary skill in the art that the components of the joint according to this invention can be secured into an operational configuration by an appropriate fastener such as a bolt (not shown) passing through the pivot pin and pivot axis to maintain the joint in an assembled configuration.

One of ordinary skill in the art will realize that the pivot pin aperture 54, tangent pin aperture 58 and pulley pin aperture 82 each permit rotation of the respective pins inserted therein while fixing the positional relationship of the pins to the respective plates. Similarly, the eccentric cam slot 64, arcuate cam slot 62 and radial slots 78 each permit the respective pins inserted therein to rotate and/or translate relative to the respective plates.

The eccentric cam slot 64 has a first end aligned on the centerline 80 of the stationary arm 74 and extends approximately 150°, in a specific presently preferred embodiment, thereby having a portion adjacent to a portion of the arcuate slot 62 without interfering therewith. As can be seen in FIGS. 1–3, the cable 12 enters the joint 10 through the bushing hole 28 and passes behind the tangent pin 32 and in front of the pivot pin 34 and is then fished behind and around the traveling pulley pin 36 and secured to the anchor pin 40. The position of the tangent pin 32 is fixed relative to the pivot pin 34 to maintain the cable 12 in contact with the pivot pin 34 as the stationary and moving arms 74, 46, respectively, are pivoted relative to each other. The arms 46 of the moving plates combine to form an extension of the joint 10 which can be easily incorporated into a rehabilitative exercise tool or other system application. Similarly, the arms 74 of the stationary plates combine to form another extension of the joint.

The angular relationship between the center pin 34 and the pulley pin 36 does not change with respect to the stationary arms 70a, 70b during operation of the joint 10. In addition, the anchor pin 40 and the center pin 34 remain aligned on the centerline 80 of the stationary arms 70a, 70b during movement of the joint 10.

In operation, the joint 10 of the present invention provides a constant torque or resistance to movement of the arms 46 of the moving plates with respect to the arms 74 of the stationary plates. The length of the cable 12 and moment arm in the joint are advantageously adjusted by the interaction of the pins and slots as the extensions are moved angularly relative to one another. The adjustment of the moment arm length compensates for the variations in the spring rate as the spring 22 is compressed from an expanded to a compact configuration.

In a preferred embodiment of the invention, the range of movement of the moving arms 46 relative to the stationary arms 74 is approximately 150° beginning at a closed position of approximately 65° angular separation (FIG. 5C) between the extensions and terminating at about 215° angular separation in an open position. In the open position, as shown in FIG. 5A, the extensions are spaced angularly approximately 215° apart. The anchor pin 40 is positioned within the eccentric cam slot 64 at one end thereof on the centerline 80 of the stationary arms 74. In addition, the anchor pin 40 is positioned within the radial slot 78 at the maximum distance away from the pivot pin 34 and pivot axis 56 thereby providing a longer moment arm in the joint. The pulley pin 36 is positioned approximately 150° from the centerline 60 of the moving arms 46 at one end of the arcuate cam slot 62. In the open position, the spring 22 is in its most relaxed configuration with the abutment plate 26 being spaced a maximum distance away from the stop 20.

As the extensions of the joint 10 are pivoted from the open position toward the closed position, the length of the cable 12 extending from the joint will be shortened thereby compressing the spring 22 and shortening the distance between the stop 20 and the movable abutment 26. As shown in FIG. 5B, as the moving arms 46 are pivoted toward the stationary arms 74 and away from the open position, the pulley pin 36 travels along the arcuate slot 62 toward the centerline 60 of the moving arms 46. The anchor pin 40 travels along the eccentric cam slot 64 and the radial slot 78 and moves closer to the pivot pin 34 shortening the moment arm. The pulley pin 36 maintains a constant spacing from the pivot axis 56 and pivot pin 34 of the joint 10 as it travels within the arcuate slot 62. As the extensions are collapsed toward the closed position, the anchor pin 40 moves within the radial 78 and eccentric slots 64 toward the pivot axis 56.

The joint 10 is shown in the closed position in FIG. 5C with the anchor pin 40 at the respective ends of eccentric cam 64 and radial slots 78. The pulley pin 36 is at the end of the arcuate slot 62 proximate the centerline 60 of the moving arms 46 in the closed position. The separation between the pivot and anchor pins, and consequently the moment arm, is the smallest in the closed position. As a result of the interaction between the cable, the pins in their respective slots and apertures, and the spring, a constant torque or resistance to angular movement is provided by the joint of this invention. The torque or resistance to movement at any angular separation of the extensions is a constant thereby providing a useful and beneficial exercise tool for the rehabilitation of injuries to human joints such as knees, elbows or the like.

It will be appreciated that the invention provides a constant torque or constant resistance joint 10, which has a particular useful application in anatomical braces, such as for the elbow. In a preferred embodiment of the invention, the constant torque is produced in part by the wrapping of the torque cable 12 about the pivot pin 34 within the joint 10 and the compensation provided by the movable anchor pin 40. The length of the cable 12 is preferentially adjusted by means of the floating anchor pin 40, so that its relative length can be varied, depending on the position of the anchor pin 40, which in itself is a function of the range of motion of the joint 10 so that the vagaries of the spring 22 powering the cable 12 and of the remainder of the system can be taken into account and eliminated to result in a constant torque joint 10. It should also be appreciated that the constant torque or constant resistance joint 10 may have application in other fields other than anatomical braces for skeletal, muscular, or nervous system rehabilitation devices.

DESIGN PROCESS FOR CONSTANT TORQUE COMPENSATION IN A JOINT

The design process for a joint according to this invention which has a constant torque compensator is initially dependent upon a number of factors which are typically provided by the physical therapist, device manufacturer, rehabilitation specialist, or the like. In particular, the range of motion of a device according to this invention is dependent upon the particular human joint or exercise program for which it will be used. For example, the rehabilitation of an elbow joint may require a constant torque over a range of 150° between 65° and 215°; whereas a knee joint may require a range of only 135° between 45° and 180°. Therefore, the range of motion must be provided to the designer.

Next, the magnitude of the torque resistance that a device provides during the exercise must be provided to the designer. For example, rehabilitation of the elbow joint might require a constant torque resistance of 0.5 ft-lbf over the range of 150° but a knee joint may require much more resistance. Furthermore, the particular distance the extension arms of the joint will be attached to the user must be determined. For example, each extension arm from the joint might be attached to the user's upper and lower arm 6 inches away from the elbow joint but a different device may be attached 10 inches on either side of the knee. Next, these parameters must be translated to the size of the device, a spring design selected, the vagaries of the particular spring selected determined, and the compensation for these vagaries calculated and applied to the joint according to this invention.

The maximum spring force and minimum spring load are factors which must be provided in the design of the joint.

The maximum spring force is that which should be produced by the device with the joint in the closed position and the minimum spring force is that which is produced at maximum separation between joint extensions in the open position.

Another factor important for the design of a joint is the physical constraints of the actual device. The maximum allowable diameter and length of the spring are factors which must be incorporated into a rehabilitation exercise device while still providing the required spring force resistance over the entire range of motion.

Next, one must determine the preload on the spring to give sufficient spring force through the entire range of motion of the joint. The diameter of the pivot pin is then selected in order to give an appropriate wrapped cable length about the pivot pin that is within the desired range of deflection of the spring. The cable wrap about the pin can be determined by the portion of the outer circumference of the cable which contacts the pin over the range of motion of the joint. The spring wrap distance around the pivot pin is equal to the change in the moment arm or the distance the anchor pin travels within the radial slot.

The spring rate must then accurately be determined over the deflection range for this particular joint. To determine the accurate spring deflection rates over the deflection range, a statistically sufficient number of springs of this design must be tested. For example, the required load for each 0.1 inches of deflection of the spring over the deflection range is measured and plotted as a curve for this particular spring design. The plot of deflection versus pounds of force is not linear due to the vagaries of the spring design and manufacture.

Given the spring rate curve and the radius arm lengths determined by the anchor pin at the maximum and minimum loads, a second spring rate curve is generated to compensate for the geometry of the cable extending from the pulley pin to the anchor at the various anchor pin locations. The force applied on the anchor pin in the closed position is perpendicular to the moment arm between the pivot pin and the anchor pin. However, as the moment arm distance increases and the anchor pin moves within the radial slot away from the pivot pin, the force of the cable upon the anchor pin is no longer perpendicular to the moment arm and a non-perpendicular component of the force is introduced as a result. Standard vector analysis as would be known by one of ordinary skill in the art can be used to arrive at a compensated spring rate curve.

Through known mathematical analysis including computer aided design programs and the like, the compensated spring rate curve is then approximated to give a best fit approximation with the least amount of variation between the plot and the compensated spring rate curve. Preferably, the appropriations of the plot should be less than the manufacturing tolerances of the joint. The resulting curve is then mapped onto the moving plate to define the eccentric cam slot according to this invention. The difference between the closest and furthest points of the anchor pin within the eccentric slot relative to the pivot pin define the length of the radial slot.

Further theoretical vagaries can be accounted for and compensated for in the design process of the joint according to this invention. For example, the cable wrap about the pulley pin is another factor which could be compensated for in the above described design process. A further factor which can be compensated for is the friction forces within the joint of the cable and the various pivot pins within the slots and pivot apertures of the joint. Anti-friction coatings such as teflon washers are preferably included into the manufacturing process of the components of a joint according to this invention.

From the above disclosure of the general principles of the present invention and the preceding detailed description of a preferred embodiment, those skilled in the art will readily comprehend the various modifications to which the present invention is susceptible. For example, other energy devices may be substituted for the spring in the constant torque joint and be within the scope of this invention. Therefore, I desire to be limited only by the scope of the following claims and equivalents thereof.

I claim:

1. A constant torque joint comprising:

first and second brace extensions;

a joint coupling said extensions together for angular rotation with respect to each other;

a cable extending from said joint, a part of said cable defining a moment art length; and a spring attached to one end of said cable, said spring having defined spring performance characteristics;

said joint further comprising:

a pivot pin, a pulley pin, and an anchor pin, said cable being maintained in contact with said pivot pin and being at least partially wrapped around said pulley pin;

an arcuate slot in said joint capturing said pulley pin;

a cam slot and a radial slot each in said joint and capturing said anchor pin;

said arcuate and cam slots each being oriented in respective angles about a joint axis of said joint, a configuration of each said arcuate and cam slot being a function of said defined spring performance characteristics, said pulley pin maintaining a generally constant distance from said joint axis while travelling within said arcuate slot, a distance from said anchor pin to said joint axis corresponding to said moment arm length varying as said anchor pin travels within said cam and radial slots; and another end of said cable being secured to said anchor pin, said cable being wrapped at least partially about said pivot and pulley pins so that upon rotation of said first and second extensions relative to each other said pulley pin travels within said arcuate slot and said anchor pin travels within said cam and radial slots to vary said moment arm length and compensate for vagaries of said defined spring performance characteristics and produce a constant torque in said joint and between said joint extensions throughout the full range of movement of said extensions with respect to each other.

2. The joint of claim 1 wherein said extensions are movable through an arc of about 150° with respect to each other.

3. The joint of claim 2 wherein said joint extensions are movable with respect to each other to and between a closed position of about 65° of angular separation and an open position of about 215° of angular separation between said joint extensions.

4. The joint of claim 1 wherein said pulley pin is located in varying positions along said arcuate slot corresponding to various positions of said joint extensions.

5. The joint of claim 1 wherein a configuration of said cam slot is a function of said spring performance for a plurality of positions of said anchor pin along said cam slot corresponding to the full range of movement of said joint extensions.

6. The joint of claim 1 wherein said spring is compressed as said brace extensions move from an open position toward a closed position, said brace extensions having a smaller angular separation in said closed position than said open position.

7. The joint of claim 1 further comprising:
a tangent pin being positioned in said joint to maintain said cable in contact with said pivot pin while said brace extensions are moved relative to each other.

8. The joint of claim 1 wherein said joint further comprises first and second plates, each said plate including one of said brace extensions, said first plate having an aperture for said pivot pin and said arcuate and cam slots therein, said second plate having individual apertures for said pivot, pulley and anchor pins and said radial slot therein.

9. The joint of claim 1 wherein said spring is mounted between a fixed stop and a movable abutment spaced from said stop, said cable one end being fixed to said abutment so that said abutment moves closer to said stop and compresses said spring when said brace extensions are rotated toward each other with a smaller angular separation therebetween.

10. The joint of claim 9 wherein said stop is fixed to one of said brace extensions.

11. The joint of claim 1 wherein said radial slot is generally linear and extends along a radius projecting from said pivot axis, said radial slot being aligned along a centerline of one of said brace extensions.

12. A joint to provide for constant torque pivotal movement between a pair of extensions, said joint comprising:

a first and a second plate juxtapositioned to each other, one of the extensions projecting from each said plate;

a cable extending from the joint, a part of said cable defining a moment arm length;

a spring attached to one end of said cable, said spring having defined spring performance characteristics;

a pivot pin, a pulley pin, and an anchor pin, said cable being maintained in contact with said pivot pin and being at least partially wrapped around said pulley pin;

an arcuate slot in said first plate, said arcuate slot capturing said pulley pin;

a cam slot in said first plate and a radial slot in said second plate, said cam and radial slots each capturing said anchor pin;

said arcuate and cam slots each being oriented in respective angles about a joint axis of said joint, a configuration of each arcuate and cam slot being a function of said defined spring performance characteristics, said pulley pin maintaining a generally constant distance from said joint axis while travelling within said arcuate slot in response to movement of the extensions relative to each other, a distance from said anchor pin to said joint axis corresponding to said moment arm length varying as said anchor pin travels within said cam and radial slots in response to movement of the extensions relative to each other; and another end of said cable being secured to said anchor pin, said cable being wrapped at least partially about said pivot and pulley pins so that upon movement of the extensions relative to each other said pulley pin travels within said arcuate slot and said anchor pin travels within said cam and radial slots to vary said moment arm length and compensate for vagaries of said defined spring performance characteristics and produce a constant torque in the joint and between the extensions throughout the full range of movement of the extensions.

13. The joint of claim 12 wherein the extensions are movable with respect to each other to and between a closed position and an open position wherein the joints have greater angular separation in said open position than in said closed position.

14. The joint of claim 12 wherein said pulley pin is located in varying positions along said arcuate slot corresponding to various positions of the extensions.

15. The joint of claim 12 wherein the configuration of said cam slot is a function of said spring performance for a plurality of positions of said anchor pin along said cam slot corresponding to the full range of movement of the extensions.

16. The joint of claim 13 wherein said spring is compressed as the extensions move from said open position toward said closed position.

17. The joint of claim 12 further comprising:
a tangent pin positioned to maintain said cable in contact with said pivot pin while the extensions move relative to each other.

18. The joint of claim 12 wherein said spring is mounted between a fixed stop and a movable abutment spaced from said stop, said cable one end being fixed to said abutment so that said abutment moves closer to said stop and compresses said spring when the extensions are rotated toward each other with a smaller angular separation therebetween.

19. The joint claim 18 wherein said stop is fixed to one of the extensions.

20. The joint of claim 12 wherein said radial slot is generally linear and extends along a radius emanating from said pivot axis, said radial slot being aligned along a centerline of one of the extensions.

21. A joint to provide for constant torque pivotal movement between a pair of extensions, said joint comprising:

a cable extending from the joint;

a spring attached to one end of said cable said spring being mounted between a movable abutment and a stop, said stop being fixed relative to one of said extensions, said one end of said cable being secured to said abutment;

a pivot pin, a pulley pin, and an anchor pin, said cable being maintained in contact with said pivot pin and being at least partially wrapped around said pulley pin;

an upper and a lower moving plate, said spring and said cable being positioned between said moving plates, each said moving plate having an arm extending from a generally circular portion, each said moving plate circular portion having an arcuate slot capturing said pulley pin, a cam slot capturing said anchor pin and a pivot aperture capturing said pivot pin, said arms of said upper and lower moving plates being aligned with each other to form one of the extensions;

a bushing positioned between said upper and lower moving plates, said upper and lower moving plates being fixed with respect to each other and with respect to said bushing;

an upper and a lower stationary plate, each said stationary plate having an arm extending from a generally circular portion, each said stationary plate having a radial slot capturing said anchor pin, said pulley pin being fixed relative to said stationary plates, said moving plates and said bushing being positioned between said stationary plates, said arms of said upper and lower stationary plates being aligned with each other to form the other of the extensions;

said arcuate slots and said cam slots each being oriented in respective angles about a joint axis of the joint, said pulley pin maintaining a generally constant distance from said joint axis while travelling within said arcuate slots in response to movement of the extensions relative to each other, a distance from said anchor pin to said joint axis varying as said anchor pin travels within said cam and radial slots in response to movement of the extensions relative to each other; and another end of said cable being secured to said anchor pin, said cable being wrapped at least partially about said pivot and pulley pins so that upon; movement of the extensions relative to each other said pulley pin travels within said arcuate slot and said anchor pin travels within said cam and radial slots to compress said spring and produce a constant torque in the joint and between the extensions throughout the full range of movement of the extensions.

22. The joint of claim 21 further comprising:

a tangent pin being fixed relative to said moving plates and positioned to maintain said cable in contact with said pivot pin while the extensions move relative to each other.

23. The joint of claim 21 wherein said radial slot is generally linear and extends along a radius projecting from said pivot axis, said radial slot being aligned along a centerline of one of the extensions.

24. The joint of claim 21 further comprising:

an upper and a lower cap plate, said bushing, moving plates and stationary plates being positioned between said cap plates, said cap plates being fixed relative to said stationary plates.

25. The joint of claim 21 wherein the extensions are movable with respect to each other to and between a closed position at about 65° of angular separation and an open position at about 215° of angular separation.

26. A constant torque joint comprising;

a joint having a pivot axis;

a cable mounted in said joint for applying resistance to movement of said joint;

a spring coupled to a first end of said cable;

a cable anchor attached to a second end of said cable and movable within said joint as a function of a spring rate of said spring over a deflection range of said spring to provide a constant torque in response to movement of said joint;

said cable having a moment arm length which varies with the movement of said cable anchor to compensate for vagaries of said spring; and an anchor pin captured in said joint, said moment arm length being defined by a position of said anchor pin relative to said pivot axis of said joint.

27. The joint of claim 26 wherein said moment arm length equals a distance between said cable anchor and said pivot axis of the joint.

28. The joint of claim 26 wherein the movement of said cable anchor is a further function of a non-linear performance of said spring rate over said deflection range.

29. A constant torque joint comprising:

a joint having a pivot axis;

a cable mounted in said joint for applying resistance to movement of said joint;

a tensioning apparatus for applying tension to said cable, said tensioning apparatus having a deflection range and a force rate;

a cable anchor attached to said cable and movable within said joint as a function of said force rate over said deflection range of said tensioning apparatus to provide a constant torque in response to movement of said joint;

said cable having a moment arm length which varies with the movement of said cable anchor to compensate for vagaries of said tensioning apparatus; and an anchor pin captured in said joint, said moment arm length being defined by a position of said anchor pin relative to said pivot axis of said joint.

* * * * *